US00PP09651P

United States Patent [19]

Pouw

[11] Patent Number: Plant 9,651

[45] Date of Patent: Oct. 1, 1996

[54] MINIATURE ROSE PLANT NAMED 'RUIPATCRU'

[75] Inventor: Antoniu A. Pouw, Hazerswoude, Netherlands

[73] Assignee: De Ruiter's Nieuwe Rozen B.V., Hazerwoude, Netherlands

[21] Appl. No.: 550,190

[22] Filed: Oct. 30, 1995

[51] Int. Cl.[6] ..... A01H 5/00

[52] U.S. Cl. ..... Plt./9

[58] Field of Search ..... Plt./7.1, 9, 10

*Primary Examiner*—Howard J. Locker
*Attorney, Agent, or Firm*—C. A. Whealy

[57] ABSTRACT

A distinctive cultivar of miniature rose plant named Ruipatcru, characterized by its large dark pink flowers; numerous flowers per plant; numerous petals per flowers; good spray formation; large leaves and leaflets; and long shelf-life.

1 Drawing Sheet

The present invention relates to a new and distinct cultivar of the miniature rose class, botanically known as *Rosa hybrida*, and hereinafter referred to by the cultivar name Ruipatcru.

The new cultivar is a product of a planned breeding program conducted by the inventor in Hazerswoude, The Netherlands. The objective of the breeding program was to develop compact pot rose varieties with garden performance that can be asexually reproduced by cuttings. The new cultivar originated from a cross made by the inventor in 1991 of two unnamed proprietary seedlings. The cultivar Ruipatcru was discovered and selected by the inventor as a flowering plant within the progeny of the stated cross in a controlled environment in Hazerswoude, The Netherlands.

Asexual reproduction of the new cultivar by cuttings taken at Hazerswoude, The Netherlands, has shown that the unique features of this new miniature rose plant are stable and reproduced true to type in successive generations of asexual reproduction.

The following traits have been repeatedly observed and are determined to be the unique characteristics of Ruipatcru. These characteristics in combination distinguish the new miniature rose plant as a new and distinct cultivar;

1. Large dark pink flowers.
2. Numerous flowers per plant.
3. Numerous petals per flower.
4. Good spray formation.
5. Large leaves and leaflets.
6. Long shelf-life.

The new miniature rose plant has not been observed under all possible environmental conditions. The phenotype may vary significantly with variations in environment such as temperature and light level, without, however, any variance in genotype.

The accompanying colored photograph illustrates typical specimens of the vegetative growth and flowers of the new miniature rose plant, showing the colors as true as it is reasonably possible to obtain in colored reproductions of this type. The photograph comprises a top perspective view of a typical plant of the new miniature rose plant grown in Hazerswoude, The Netherlands.

The following observations, measurements, values, and comparisons describe plants grown in Hazerswoude, The Netherlands, under glass covering with average day temperature of 20° C, average night temperatures of 16° to 18° C, and average light level of 2,000 J/cm$^2$.

In the following description, color reference are made to The Royal Horticultural Society Colour Chart except where general terms of ordinary dictionary significance are used.

Classification:

*Botanical.*—*Rosa hybrida* cultivar Ruipatcru.

*Commercial.*—Miniature pot rose.

Parentage:

*Male or pollen parent.*—Unnamed proprietary seedling.

*Female or seed parent.*—Unnamed proprietary seedling.

Plant description:

*Form.*—Rounded form, uniform, and spreading.

*Growth habit.*—Moderately vigorous, yet compact. Freely branching, dense growth. Suitable for 10 - cm containers. Time to produce a finished plant in a 10 - cm container 20 to 30 cm in height is generally 10 to 12 weeks depending on average temperature, light level, and cultural practices.

*Stem and lateral branches.*—Quantity of lateral branches from pinching: Generally three. Length of lateral branches: 1 to 5 cm. Color: Immature stems: 138B. Mature stems: 137A.

*Foliage description.*—Leaves arranged alternately, compound with three to seven leaflets per leaf, generally symmetrical, abundant, and flat in aspect. Stipules at leaf base. Quantity: Five to eight per lateral branch. Leaf size: Length:10 cm. Width: 5 cm. Leaflet size: Length: 1.5 2.5 cm. Width: 1 to 2 cm. Shape: Ovate with acute tip and obtuse base. Texture: Smooth and leathery. Margin: Serrate. Petiole length: 4 cm. Color: Young foliage, upper side: 143B. Young foliage, under side: 144B. Mature foliage, upper side: 137A. Mature foliage, under side: 138A. Petiole: Immature foliage: 138B. Mature foliage: 137A. Stipule: Immature foliage: 138B. Mature foliage: 137A. Venation, upper side: 138B. Venation, under side: 138B.

*Prickles.*—Located on petioles and stems. Length: 0.1 to 0.3 cm.

Flower description:

*Flower type and habit.*—Large dark pink flowers. Consistently symmetrical rosette flowers that are flat in aspect. Freely and continuously flowering. The flowers are borne singly on peduncles and arranged in clusters of up to nine flowers each. There are numerous sprays per plant.

*Flowering season.*—Year-round under greenhouse conditions, optimal flowering during summer and autumm in the Northern Hemisphere.

*Flower diameter.*—3 to 4 cm.

*Flower depth (height).*—1 to 2 cm.

*Flower longevity on plant.*—22 days.

*Fragrance.*—None.

*Persistent.*—Yes.

*Flower buds.*—Shape: Ovoid. Size: Length: 1 to 2 cm. Width: 0.5 to 1 cm. Color: 52B.

*Petals.*—Quantiy: At least 95 per flower. Arrangement: Nineteen rows of petals with five petals each. Size: Length: 1 to 2 cm. Width: 0.5 to 1.5 cm. Shape: Elliptical with obtuse tip. Texture: Smooth and satiny. Margin: Entire. Color: When opening: 52A and 52B. Upper side, mature: 52D. Under side, mature: 50D. Fade: Upper and under sides do not fade, but maintain color.

*Petaloids.*—Quantiy: At least 120 per flower. Arrangement: Twenty-four rows of petals with five petaloids each. Size: Length: 0.5 to 1 cm. Width: 0.2 to 0.5 cm. Shape: Elliptical with obtuse tip. Texture: Smooth and satiny. Margin: Entire. Color: Immature: 50B. Mature: 52D.

*Sepals.*—Quantity: Five per flower Arrangement: One row with five sepals. Shape: Ovate with acute tip. Color: Upper side: 138A. Under side: 138B.

*Calyx.*—Almost inconspicuous. Shape: Funnel. Color: 143C.

*Peduncles.*—Strong and erect, pubescent. Length: 3.5 cm. Color: 143C and 143B.

*Reproductive organs.*—Stamens: Quantity: 5 to 10 per flower. Anther size: 0.1 to 0.2 cm. Anther shape: Oblong. Anther color: 164B. Pistils: Quantity: 60 to 90 per flower. Style length: 0.2 cm. Style color: 52B. Stigma color: 145D.

Disease resistance: No resistance or susceptibility observed.

Seed production: Seed production is rarely observed.

It is claimed:

1. A new and distinct miniature rose plant named Ruipatcru, as illustrated and described.

* * * * *

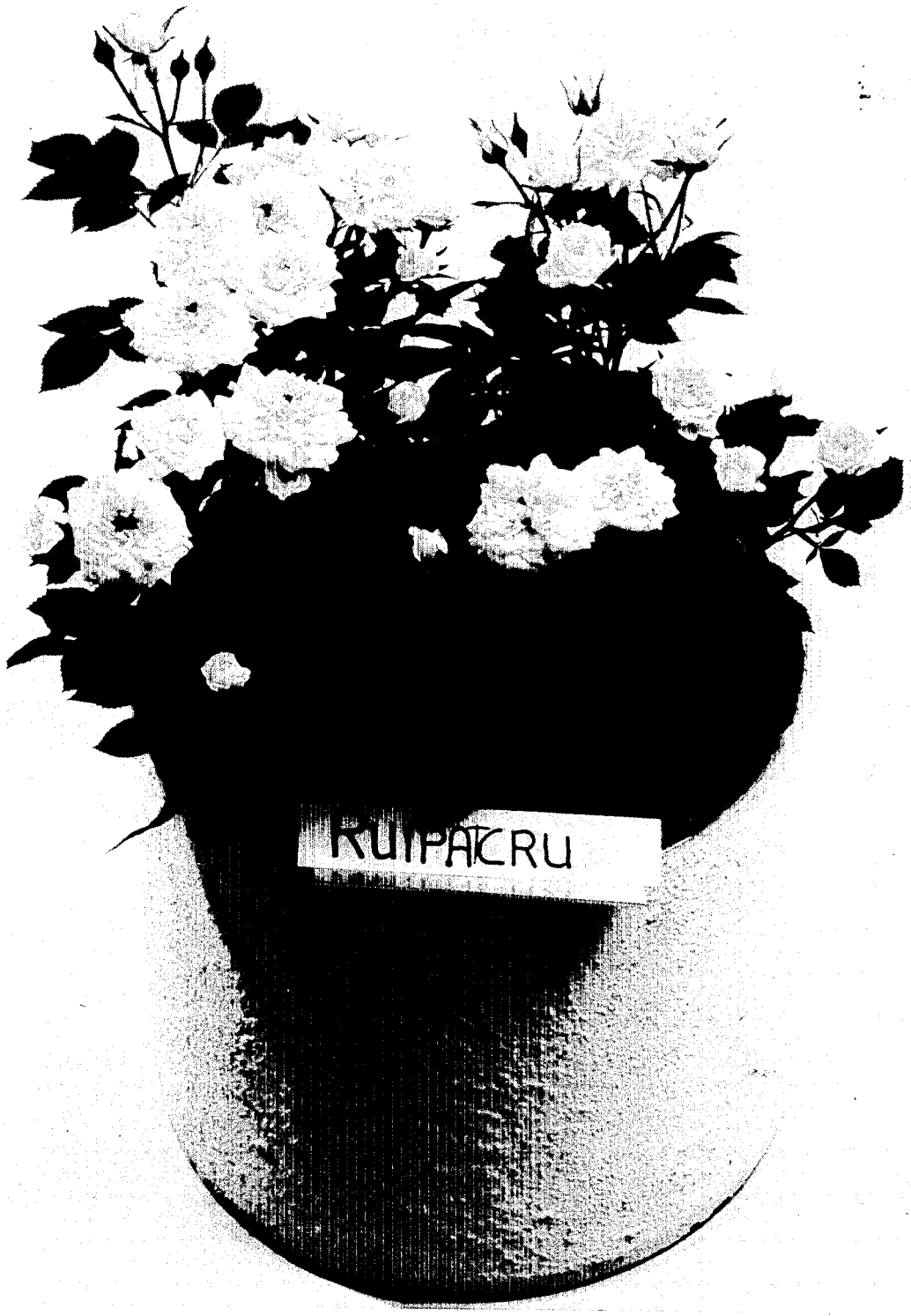
KUIPACRU